(12) United States Patent
Reggiardo et al.

(10) Patent No.: US 7,756,561 B2
(45) Date of Patent: Jul. 13, 2010

(54) METHOD AND APPARATUS FOR PROVIDING RECHARGEABLE POWER IN DATA MONITORING AND MANAGEMENT SYSTEMS

(75) Inventors: Christopher V. Reggiardo, Castro Valley, CA (US); Martin J. Fennell, Concord, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 0 days.

(21) Appl. No.: 11/240,273

(22) Filed: Sep. 30, 2005

(65) Prior Publication Data

US 2007/0078323 A1   Apr. 5, 2007

(51) Int. Cl.
*A61B 5/00* (2006.01)
(52) U.S. Cl. .................. 600/347; 600/345; 600/365
(58) Field of Classification Search .................. 600/300, 600/301, 309, 365
See application file for complete search history.

(56) References Cited

U.S. PATENT DOCUMENTS

| | | | |
|---|---|---|---|
| 2,915,579 A | 12/1959 | Mendelsohn | |
| 3,750,687 A | 8/1973 | Williams | |
| 3,843,455 A | 10/1974 | Bier | |
| 3,930,493 A | 1/1976 | Williamson | |
| 3,994,799 A | 11/1976 | Yao et al. | |
| 4,018,547 A | 4/1977 | Rogen | |
| 4,121,282 A | 10/1978 | Ohsawa | |
| 4,193,397 A | 3/1980 | Tucker et al. | |
| 4,268,173 A | 5/1981 | Barnard et al. | |
| 4,401,122 A | 8/1983 | Clark, Jr. | |
| 4,439,197 A | 3/1984 | Honda et al. | |
| 4,447,224 A | 5/1984 | DeCant, Jr. et al. | |
| 4,458,686 A | 7/1984 | Clark, Jr. | |
| 4,467,811 A | 8/1984 | Clark, Jr. | |
| 4,494,950 A | 1/1985 | Fischell | |
| 4,512,348 A | 4/1985 | Uchigaki et al. | |

(Continued)

FOREIGN PATENT DOCUMENTS

EP     0455455     11/1991

(Continued)

OTHER PUBLICATIONS

International Search Report and Written Opinion of the International Searching Authority for International Application No. PCT/US2006/037314 filed Sep. 25, 2008 to Abbott Diabetes Care, Inc.

(Continued)

*Primary Examiner*—Robert L Nasser
(74) *Attorney, Agent, or Firm*—Jackson & Co., LLP

(57) ABSTRACT

Method and apparatus for providing a disposable power supply source integrated into the housing of the transmitter unit mount that is placed on the skin of the patient, and configured to receive the transmitter unit is disclosed. The transmitter unit mount is configured to be disposable with the analyte sensor so that power supply providing power to the transmitter unit is also replaced. The transmitter unit may include a rechargeable battery that is recharged by the power supply unit of the transmitter unit mount when the transmitter is mounted to the transmitter unit mount. Other energy store configurations including single large capacitor (supercap) or a capacitor and DC/DC converter configurations are disclosed.

19 Claims, 5 Drawing Sheets

U.S. PATENT DOCUMENTS

| | | |
|---|---|---|
| 4,531,235 A | 7/1985 | Brusen |
| 4,563,249 A | 1/1986 | Hale |
| 4,570,492 A | 2/1986 | Walsh |
| 4,633,878 A | 1/1987 | Bombardieri |
| 4,686,624 A | 8/1987 | Blum et al. |
| 4,850,959 A | 7/1989 | Findl |
| 4,851,827 A | 7/1989 | Nicholas |
| 4,866,396 A | 9/1989 | Tamura |
| 4,890,621 A | 1/1990 | Hakky |
| 4,953,552 A | 9/1990 | DeMarzo |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,190,041 A | 3/1993 | Palti |
| 5,207,666 A | 5/1993 | Idriss et al. |
| 5,211,371 A | 5/1993 | Coffee |
| 5,211,626 A | 5/1993 | Frank et al. |
| 5,262,305 A | 11/1993 | Heller et al. |
| 5,278,997 A | 1/1994 | Martin |
| 5,291,887 A | 3/1994 | Stanley et al. |
| 5,324,599 A | 6/1994 | Oyama et al. |
| 5,325,280 A | 6/1994 | Tortola et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,494,562 A | 2/1996 | Maley et al. |
| 5,497,772 A | 3/1996 | Schulman et al. |
| 5,507,288 A | 4/1996 | Bocker et al. |
| 5,517,434 A | 5/1996 | Hanson et al. |
| 5,559,528 A | 9/1996 | Ravid |
| 5,568,400 A | 10/1996 | Stark et al. |
| 5,575,770 A | 11/1996 | Melsky et al. |
| 5,593,852 A | 1/1997 | Heller et al. |
| 5,594,906 A | 1/1997 | Holmes, II et al. |
| 5,604,404 A | 2/1997 | Sahara |
| 5,615,671 A | 4/1997 | Schoonen et al. |
| 5,622,413 A | 4/1997 | Kim et al. |
| 5,622,482 A | 4/1997 | Lee |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,671,301 A | 9/1997 | Kuperschmidt |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,873,026 A | 2/1999 | Reames |
| 5,885,211 A | 3/1999 | Eppstein et al. |
| 5,899,855 A | 5/1999 | Brown |
| 5,913,833 A | 6/1999 | Elstrom et al. |
| 5,923,512 A | 7/1999 | Brownlow et al. |
| 5,947,921 A | 9/1999 | Johnson et al. |
| 5,948,512 A | 9/1999 | Kubota et al. |
| 5,951,836 A | 9/1999 | McAleer et al. |
| 5,954,643 A | 9/1999 | Van Antwerp et al. |
| 5,965,380 A | 10/1999 | Heller et al. |
| 5,971,922 A | 10/1999 | Arita et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,496 A | 2/2000 | Loomis et al. |
| 6,027,692 A | 2/2000 | Galen et al. |
| 6,032,059 A | 2/2000 | Henning et al. |
| 6,041,253 A | 3/2000 | Kost et al. |
| 6,041,665 A | 3/2000 | Hussain |
| 6,059,546 A | 5/2000 | Brenan et al. |
| 6,063,039 A | 5/2000 | Cunningham et al. |
| 6,064,368 A | 5/2000 | Kang |
| 6,066,243 A | 5/2000 | Anderson et al. |
| 6,067,017 A | 5/2000 | Stewart et al. |
| 6,067,463 A | 5/2000 | Jeng et al. |
| 6,071,249 A | 6/2000 | Cunningham et al. |
| 6,071,251 A | 6/2000 | Cunningham et al. |
| 6,073,031 A * | 6/2000 | Helstab et al. .............. 455/557 |
| 6,077,660 A | 6/2000 | Wong et al. |
| 6,081,104 A | 6/2000 | Kern |
| 6,083,710 A | 7/2000 | Heller et al. |
| 6,085,871 A | 7/2000 | Karamata |
| 6,091,975 A | 7/2000 | Daddona et al. |
| 6,093,156 A | 7/2000 | Cunningham et al. |
| 6,121,009 A | 9/2000 | Heller et al. |
| 6,129,823 A | 10/2000 | Hughes et al. |
| 6,132,371 A | 10/2000 | Dempsey et al. |
| 6,142,939 A | 11/2000 | Eppstein et al. |
| 6,144,303 A | 11/2000 | Federman |
| 6,144,869 A | 11/2000 | Berner et al. |
| 6,144,922 A | 11/2000 | Douglas et al. |
| 6,154,855 A | 11/2000 | Norman |
| 6,155,992 A | 12/2000 | Henning et al. |
| 6,157,442 A | 12/2000 | Raskas |
| 6,160,449 A | 12/2000 | Klomsdorf et al. |
| 6,162,202 A | 12/2000 | Sicurelli et al. |
| 6,162,611 A | 12/2000 | Heller et al. |
| 6,164,284 A | 12/2000 | Schulman et al. |
| 6,173,160 B1 | 1/2001 | Liimatainen |
| 6,175,752 B1 | 1/2001 | Say et al. |
| 6,180,416 B1 | 1/2001 | Kurnik et al. |
| 6,185,452 B1 | 2/2001 | Schulman et al. |
| 6,201,980 B1 | 3/2001 | Darrow et al. |
| 6,206,841 B1 | 3/2001 | Cunningham et al. |

| Patent No. | Date | Inventor(s) |
|---|---|---|
| 6,208,894 B1 | 3/2001 | Schulman et al. |
| 6,212,416 B1 | 4/2001 | Ward et al. |
| 6,222,514 B1 | 4/2001 | DeLuca |
| 6,232,370 B1 | 5/2001 | Kubota et al. |
| 6,233,471 B1 | 5/2001 | Berner et al. |
| 6,242,961 B1 | 6/2001 | Liu et al. |
| 6,245,060 B1 | 6/2001 | Loomis et al. |
| 6,248,067 B1 | 6/2001 | Causey, III et al. |
| 6,262,708 B1 | 7/2001 | Chu |
| 6,272,364 B1 | 8/2001 | Kurnik |
| 6,278,425 B1 | 8/2001 | DeLuca |
| 6,280,587 B1 | 8/2001 | Matsumoto |
| 6,283,926 B1 | 9/2001 | Cunningham et al. |
| 6,284,478 B1 | 9/2001 | Heller et al. |
| 6,295,506 B1 * | 9/2001 | Heinonen et al. ........... 702/104 |
| 6,298,254 B2 | 10/2001 | Tamada |
| 6,298,255 B1 | 10/2001 | Cordero et al. |
| 6,299,578 B1 | 10/2001 | Kurnik et al. |
| 6,301,499 B1 | 10/2001 | Carlson et al. |
| 6,306,104 B1 | 10/2001 | Cunningham et al. |
| 6,309,351 B1 | 10/2001 | Kurnik et al. |
| 6,312,888 B1 | 11/2001 | Wong et al. |
| 6,315,721 B2 | 11/2001 | Schulman et al. |
| 6,326,160 B1 | 12/2001 | Dunn et al. |
| 6,329,161 B1 | 12/2001 | Heller et al. |
| 6,341,232 B1 | 1/2002 | Conn et al. |
| 6,356,776 B1 | 3/2002 | Berner et al. |
| 6,360,888 B1 | 3/2002 | McIvor et al. |
| 6,366,793 B1 | 4/2002 | Bell et al. |
| 6,368,141 B1 | 4/2002 | Van Antwerp et al. |
| 6,368,274 B1 | 4/2002 | Van Antwerp et al. |
| 6,372,371 B1 | 4/2002 | Iarochenko et al. |
| 6,375,344 B1 | 4/2002 | Hanson et al. |
| 6,375,638 B2 | 4/2002 | Nason et al. |
| 6,377,894 B1 | 4/2002 | Deweese et al. |
| 6,381,496 B1 | 4/2002 | Meadows et al. |
| 6,393,318 B1 | 5/2002 | Conn et al. |
| 6,403,944 B1 | 6/2002 | MacKenzie et al. |
| 6,405,066 B1 | 6/2002 | Essenpreis et al. |
| 6,408,402 B1 | 6/2002 | Norman |
| 6,417,074 B2 | 7/2002 | Kopley et al. |
| 6,419,642 B1 | 7/2002 | Marchitto et al. |
| 6,425,829 B1 | 7/2002 | Julien |
| 6,427,088 B1 | 7/2002 | Bowman, IV et al. |
| 6,432,585 B1 | 8/2002 | Kawakami et al. |
| 6,437,379 B2 | 8/2002 | Kopley et al. |
| 6,438,385 B1 | 8/2002 | Heinonen et al. |
| 6,438,414 B1 | 8/2002 | Conn et al. |
| 6,442,413 B1 | 8/2002 | Silver |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,980 B2 | 10/2002 | Sirhan et al. |
| 6,472,991 B1 | 10/2002 | Schulman et al. |
| 6,478,736 B1 | 11/2002 | Mault |
| 6,480,730 B2 | 11/2002 | Darrow et al. |
| 6,482,158 B2 | 11/2002 | Mault |
| 6,485,138 B1 | 11/2002 | Kubota et al. |
| 6,492,180 B2 | 12/2002 | Brown et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 * | 5/2003 | Causey et al. ................ 600/300 |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 * | 5/2003 | Say et al. .................... 600/365 |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnacaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,659,948 B2 | 12/2003 | Lebel et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Lebel et al. |
| 6,695,885 B2 | 2/2004 | Schulman et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,738,654 B2 | 5/2004 | Sohrab |
| 6,740,075 B2 | 5/2004 | Lebel et al. |
| 6,741,877 B1 | 5/2004 | Shults et al. |
| 6,743,635 B2 | 6/2004 | Neel et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |

| | | |
|---|---|---|
| 6,773,563 B2 | 8/2004 | Matsumoto |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,020,508 B2 | 3/2006 | Stirovic et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 * | 8/2006 | Tess et al. .................. 73/53.01 |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,225,535 B2 | 6/2007 | Feldman et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,276,029 B2 | 10/2007 | Goode, Jr. et al. |
| 7,283,867 B2 | 10/2007 | Strother et al. |
| 7,299,080 B2 | 11/2007 | Acosta et al. |
| 7,310,544 B2 | 12/2007 | Brister et al. |
| 7,323,091 B1 | 1/2008 | Gillette et al. |
| 7,324,949 B2 | 1/2008 | Bristol et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,510,526 B2 * | 3/2009 | Merry et al. .................. 600/300 |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0056255 A1 | 12/2001 | Kost et al. |
| 2002/0002326 A1 | 1/2002 | Causey, III et al. |
| 2002/0002328 A1 | 1/2002 | Tamada |

| | | |
|---|---|---|
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0177764 A1 | 11/2002 | Sohrab |
| 2002/0193679 A1* | 12/2002 | Malave et al. ............... 600/407 |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0060692 A1 | 3/2003 | Ruchti et al. |
| 2003/0060765 A1 | 3/2003 | Campbell et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnacaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0011671 A1 | 1/2004 | Shults et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0039256 A1 | 2/2004 | Kawatahara et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0263354 A1 | 12/2004 | Mann et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |

| | | | | | | |
|---|---|---|---|---|---|---|
| 2005/0051580 A1 | 3/2005 | Ramey | | 2006/0036143 A1 | 2/2006 | Brister et al. |
| 2005/0053365 A1 | 3/2005 | Adams et al. | | 2006/0036144 A1 | 2/2006 | Brister et al. |
| 2005/0054909 A1 | 3/2005 | Petisce et al. | | 2006/0036145 A1 | 2/2006 | Brister et al. |
| 2005/0059926 A1 | 3/2005 | Sage, Jr. et al. | | 2006/0036187 A1 | 2/2006 | Vos et al. |
| 2005/0065464 A1 | 3/2005 | Talbot et al. | | 2006/0040402 A1 | 2/2006 | Brauker et al. |
| 2005/0090607 A1 | 4/2005 | Tapsak et al. | | 2006/0052679 A1 | 3/2006 | Kotulla et al. |
| 2005/0090808 A1 | 4/2005 | Malave et al. | | 2006/0058602 A1 | 3/2006 | Kwiatkowski et al. |
| 2005/0112169 A1 | 5/2005 | Brauker et al. | | 2006/0058627 A1 | 3/2006 | Flaherty et al. |
| 2005/0113657 A1 | 5/2005 | Alarcon et al. | | 2006/0063218 A1 | 3/2006 | Bartowiak et al. |
| 2005/0113658 A1 | 5/2005 | Jacobson et al. | | 2006/0074564 A1 | 4/2006 | Bartkowiak et al. |
| 2005/0118726 A1 | 6/2005 | Scultz et al. | | 2006/0166629 A1 | 7/2006 | Reggiardo |
| 2005/0121322 A1 | 6/2005 | Say et al. | | 2006/0173259 A1 | 8/2006 | Flaherty et al. |
| 2005/0124873 A1 | 6/2005 | Shults et al. | | 2006/0173444 A1 | 8/2006 | Choy et al. |
| 2005/0137471 A1 | 6/2005 | Haar et al. | | 2006/0222566 A1 | 10/2006 | Brauker et al. |
| 2005/0143635 A1 | 6/2005 | Kamath et al. | | 2006/0224141 A1 | 10/2006 | Rush et al. |
| 2005/0143636 A1 | 6/2005 | Zhang et al. | | 2006/0247508 A1 | 11/2006 | Fennell |
| 2005/0148003 A1 | 7/2005 | Keith et al. | | 2006/0273759 A1 | 12/2006 | Reggiardo |
| 2005/0154271 A1 | 7/2005 | Rasdal et al. | | 2007/0002533 A1* | 1/2007 | Kogan et al. ................. 361/686 |
| 2005/0161346 A1 | 7/2005 | Simpson et al. | | 2007/0016381 A1 | 1/2007 | Kamath et al. |
| 2005/0171503 A1 | 8/2005 | Van Den Berghe et al. | | 2007/0073129 A1* | 3/2007 | Shah et al. ................... 600/365 |
| 2005/0171513 A1 | 8/2005 | Mann et al. | | 2007/0106135 A1 | 5/2007 | Sloan |
| 2005/0173245 A1 | 8/2005 | Feldman et al. | | 2007/0135697 A1 | 6/2007 | Reggiardo |
| 2005/0176136 A1 | 8/2005 | Burd et al. | | 2007/0163880 A1 | 7/2007 | Woo et al. |
| 2005/0177036 A1 | 8/2005 | Shults et al. | | 2007/0173711 A1 | 7/2007 | Shah et al. |
| 2005/0181012 A1 | 8/2005 | Saint et al. | | 2007/0176867 A1 | 8/2007 | Reggiardo et al. |
| 2005/0182306 A1 | 8/2005 | Sloan | | 2007/0203966 A1 | 8/2007 | Brauker et al. |
| 2005/0182451 A1 | 8/2005 | Griffin et al. | | 2007/0235331 A1 | 10/2007 | Simpson et al. |
| 2005/0187720 A1 | 8/2005 | Goode, Jr. et al. | | 2008/0021666 A1 | 1/2008 | Goode, Jr. et al. |
| 2005/0192557 A1 | 9/2005 | Brauker et al. | | 2008/0033254 A1 | 2/2008 | Kamath et al. |
| 2005/0195930 A1 | 9/2005 | Spital et al. | | 2008/0045824 A1 | 2/2008 | Tapsak et al. |
| 2005/0199494 A1 | 9/2005 | Say et al. | | 2008/0064941 A1 | 3/2008 | Funderburk et al. |
| 2005/0203360 A1 | 9/2005 | Brauker et al. | | 2008/0071156 A1 | 3/2008 | Brister et al. |
| 2005/0214892 A1 | 9/2005 | Kovatchev et al. | | 2008/0083617 A1 | 4/2008 | Simpson et al. |
| 2005/0215871 A1 | 9/2005 | Feldman et al. | | 2008/0086042 A1 | 4/2008 | Brister et al. |
| 2005/0215872 A1 | 9/2005 | Berner et al. | | 2008/0086044 A1 | 4/2008 | Brister et al. |
| 2005/0235732 A1 | 10/2005 | Rush | | 2008/0086273 A1 | 4/2008 | Shults et al. |
| 2005/0238503 A1 | 10/2005 | Rush et al. | | 2008/0108942 A1 | 5/2008 | Brister et al. |
| 2005/0239154 A1 | 10/2005 | Feldman et al. | | 2008/0183061 A1 | 7/2008 | Goode et al. |
| 2005/0245795 A1 | 11/2005 | Goode, Jr. et al. | | 2008/0183399 A1 | 7/2008 | Goode et al. |
| 2005/0245799 A1 | 11/2005 | Brauker et al. | | 2008/0188731 A1 | 8/2008 | Brister et al. |
| 2005/0249606 A1 | 11/2005 | Rush | | 2008/0189051 A1 | 8/2008 | Goode et al. |
| 2005/0251083 A1 | 11/2005 | Carr-Brendel et al. | | 2008/0194935 A1 | 8/2008 | Brister et al. |
| 2005/0261660 A1 | 11/2005 | Choi | | 2008/0194936 A1 | 8/2008 | Goode et al. |
| 2005/0267780 A1 | 12/2005 | Ray et al. | | 2008/0194937 A1 | 8/2008 | Goode et al. |
| 2005/0271546 A1 | 12/2005 | Gerber et al. | | 2008/0194938 A1 | 8/2008 | Brister et al. |
| 2005/0271547 A1 | 12/2005 | Gerber et al. | | 2008/0195232 A1 | 8/2008 | Carr-Brendel et al. |
| 2005/0272640 A1 | 12/2005 | Doyle, III et al. | | 2008/0195967 A1 | 8/2008 | Goode et al. |
| 2005/0272985 A1 | 12/2005 | Kotulla et al. | | 2008/0197024 A1 | 8/2008 | Simpson et al. |
| 2005/0277844 A1 | 12/2005 | Strother et al. | | 2008/0200788 A1 | 8/2008 | Brister et al. |
| 2005/0287620 A1 | 12/2005 | Heller et al. | | 2008/0200789 A1 | 8/2008 | Brister et al. |
| 2006/0001538 A1 | 1/2006 | Kraft et al. | | 2008/0200791 A1 | 8/2008 | Simpson et al. |
| 2006/0001550 A1 | 1/2006 | Mann et al. | | 2008/0208025 A1 | 8/2008 | Shults et al. |
| 2006/0001551 A1 | 1/2006 | Kraft et al. | | 2008/0214915 A1 | 9/2008 | Brister et al. |
| 2006/0003398 A1 | 1/2006 | Heller et al. | | 2008/0214918 A1 | 9/2008 | Brister et al. |
| 2006/0004271 A1 | 1/2006 | Peyser et al. | | 2008/0228051 A1 | 9/2008 | Shults et al. |
| 2006/0007017 A1 | 1/2006 | Mann et al. | | 2008/0228054 A1 | 9/2008 | Shults et al. |
| 2006/0015020 A1 | 1/2006 | Neale et al. | | 2008/0242961 A1 | 10/2008 | Brister et al. |
| 2006/0015024 A1 | 1/2006 | Brister et al. | | 2008/0262469 A1 | 10/2008 | Brister et al. |
| 2006/0016700 A1 | 1/2006 | Brister et al. | | 2008/0275313 A1 | 11/2008 | Brister et al. |
| 2006/0019327 A1 | 1/2006 | Brister et al. | | 2008/0287764 A1 | 11/2008 | Rasdal et al. |
| 2006/0020186 A1 | 1/2006 | Brister et al. | | 2008/0287765 A1 | 11/2008 | Rasdal et al. |
| 2006/0020187 A1 | 1/2006 | Brister et al. | | 2008/0287766 A1 | 11/2008 | Rasdal et al. |
| 2006/0020188 A1 | 1/2006 | Kamath et al. | | 2008/0296155 A1 | 12/2008 | Shults et al. |
| 2006/0020189 A1 | 1/2006 | Brister et al. | | 2008/0306368 A1 | 12/2008 | Goode et al. |
| 2006/0020190 A1 | 1/2006 | Kamath et al. | | 2008/0306434 A1 | 12/2008 | Dobbles et al. |
| 2006/0020191 A1 | 1/2006 | Brister et al. | | 2008/0306435 A1 | 12/2008 | Kamath et al. |
| 2006/0020192 A1 | 1/2006 | Brister et al. | | 2008/0306444 A1 | 12/2008 | Brister et al. |
| 2006/0025663 A1 | 2/2006 | Talbot et al. | | 2009/0012379 A1 | 1/2009 | Goode et al. |
| 2006/0031094 A1 | 2/2006 | Cohen et al. | | 2009/0018424 A1 | 1/2009 | Kamath et al. |
| 2006/0036139 A1 | 2/2006 | Brister et al. | | 2009/0030294 A1 | 1/2009 | Petisce et al. |
| 2006/0036140 A1 | 2/2006 | Brister et al. | | 2009/0036758 A1 | 2/2009 | Brauker et al. |
| 2006/0036141 A1 | 2/2006 | Kamath et al. | | 2009/0036763 A1 | 2/2009 | Brauker et al. |
| 2006/0036142 A1 | 2/2006 | Brister et al. | | 2009/0043181 A1 | 2/2009 | Brauker et al. |

| | | |
|---|---|---|
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |

FOREIGN PATENT DOCUMENTS

| | | |
|---|---|---|
| EP | 0878707 | 11/1998 |
| EP | 0543916 | 7/2001 |
| EP | 1130638 | 9/2001 |
| EP | 1755443 | 11/2005 |
| JP | 2001-177423 | 6/2001 |
| JP | 2001-056673 | 11/2001 |
| WO | WO-99/22236 | 5/1999 |
| WO | WO-01/52727 | 7/2001 |
| WO | WO-02/084860 | 10/2002 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/079114 | 7/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/090037 | 8/2007 |
| WO | WO-2008/055037 | 5/2008 |

OTHER PUBLICATIONS

International Preliminary Report on Patentability and Written Opinion of the International Searching Authority for International Application No. PCT/US2006/037314 filed Sep. 25, 2008 to Abbott Diabetes Care, Inc.

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

"An Electrochemical Slow Flow Meter", http://gore.ocean.washington.edu/research/slow_flow_meter.html, 2005, 3 pages.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

European Patent Application No. EP-06804124.3, Extended European Search Report mailed Nov. 20, 2009.

\* cited by examiner

METHOD AND APPARATUS FOR PROVIDING RECHARGEABLE POWER IN DATA MONITORING AND MANAGEMENT SYSTEMS

BACKGROUND

Analayte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain glucose monitoring systems include a transcutaneous or subcutaneous analyte sensor configuration which is, for example, partially mounted on the skin of a subject whose glucose level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another portion or segment of the analyte sensor is in communication with the transmitter unit. The transmitter unit is configured to transmit the analyte levels detected by the sensor over a wireless communication link such as an RF (radio frequency) communication link. To transmit signals, the transmitter unit requires a power supply such as a battery. Generally, batteries have a limited life span and require periodic replacement. More specifically, depending on the power consumption of the transmitter unit, the power supply in the transmitter unit may require frequent replacement, or the transmitter unit may require replacement (e.g, disposable power supply such as disposable battery).

This may be cumbersome and inconvenient to the patient. Moreover, in continuous glucose monitoring systems, when the transmitter unit fails to transmit the glucose data from the sensor due to power failure, the patient may be approaching a critical physiological state such as hyperglycemia or hypoglycemia with little warning or knowledge. This could potentially be fatal to the patient.

At the same time, however, it may be undesirable to limit the functions of the transmitter so as to reduce the power consumption in order to prolong the battery life of the transmitter. For example, the transmitter unit may be configured to transmit less periodically or frequently to save battery power—this may in turn potentially result in inaccurate determination of monitored glucose levels as the detected levels are not sufficiently close together to provide a comprehensive result of the continuous monitoring.

Moreover, increasing the battery size may prolong the operating life of the transmitter unit, but would result in a more physically cumbersome design, and would add extra weight to be carried by the patient which is generally undesirable.

In view of the foregoing, it would be desirable to have an approach to provide a rechargeable power supply for the transmitter unit in the data monitoring and management system such that the compact, lightweight configuration of the transmitter unit worn by the patient can be maintained. Moreover, in view of the foregoing, it would be desirable to have various options for the power supply and/or a rechargeable power supply for the transmitter unit in the data monitoring and management systems.

SUMMARY OF THE INVENTION

In view of the foregoing, in accordance with the various embodiments of the present invention, there is provided a method and apparatus for providing a disposable power supply source integrated into the housing of the transmitter unit mount that is placed on the skin of the patient, and configured to receive or "mate" with the transmitter unit. The transmitter unit mount is configured to be disposable with the analyte sensor, such that with each replacement of the analyte sensor (for example, every three or five days), the power supply providing power to the transmitter unit is also replaced.

In a further embodiment of the present invention, the transmitter unit may further be configured to include a rechargeable battery such that when the transmitter unit is mounted to the transmitter unit mount (that includes a separate disposable power supply), the power supply unit of the transmitter unit mount is configured to charge the rechargeable power supply of the transmitter unit. In this manner, the transmitter unit may be configured to maintain the communication link with the corresponding receiver unit during the period when the patient is replacing the analyte sensor (along with the transmitter unit mount).

Yet in a further embodiment of the present invention, the transmitter may be configured to include a series of capacitor combinations (and/or in conjunction with other circuitry including a corresponding series of DC/DC converters) configured to store charge so as to provide power to the transmitter. In one embodiment, the capacitor may include a single large capacitor (supercap) as energy store to provide power to the transmitter in the data monitoring and management system.

These and other objects, features and advantages of the present invention will become more fully apparent from the following detailed description of the embodiments, the appended claims and the accompanying drawings.

DETAILED DESCRIPTION

Figure 1:
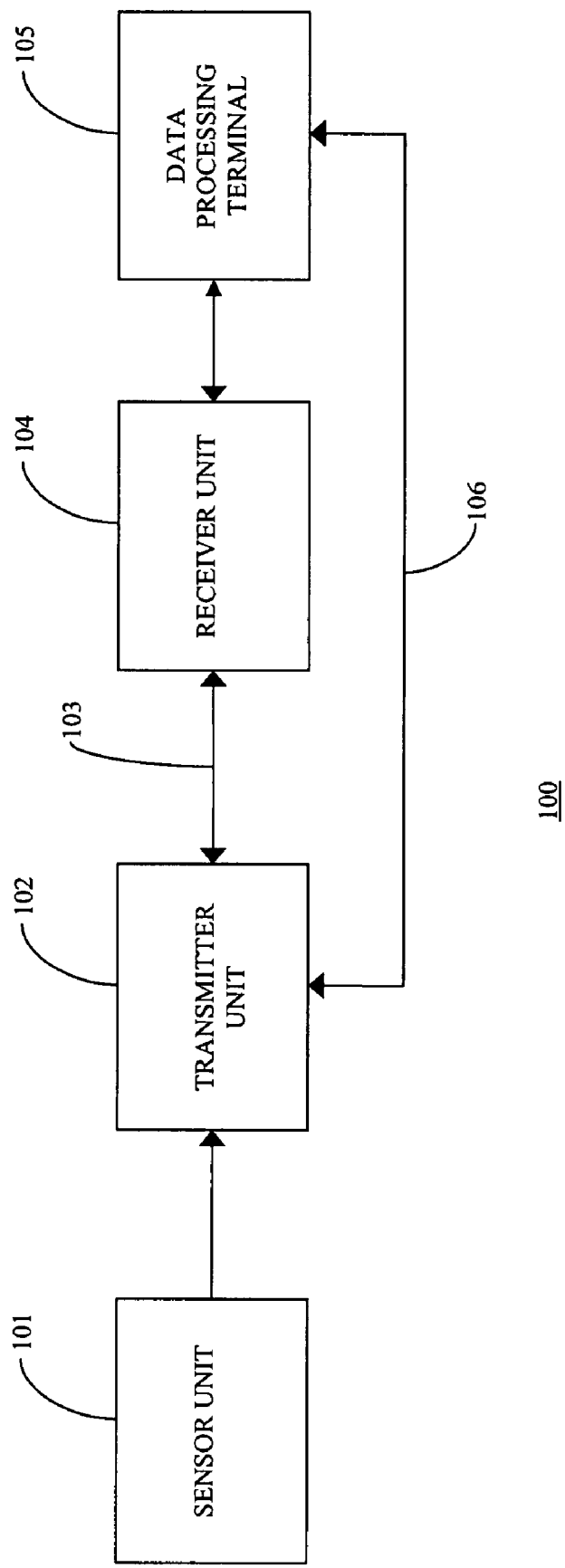
FIG. 1 illustrates a block diagram of a data monitoring and management system for practicing one embodiment of the present invention.

FIG. 1 illustrates a data monitoring and management system such as, for example, an analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Indeed, analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The glucose monitoring system 100 includes a sensor 101, a transmitter 102 coupled to the sensor 101, and a receiver 104 which is configured to communicate with the transmitter 102 via a communication link 103. The receiver 104 may be further configured to transmit data to a data processing terminal 105 for evaluating the data received by the receiver 104. Moreover, the data processing terminal in one embodiment may be configured to receive data directly from the transmitter 102 via a communication link 106 which may optionally be configured for bi-directional communication.

Only one sensor 101, transmitter 102, communication link 103, receiver 104, and data processing terminal 105 are shown in the embodiment of the glucose monitoring system 100 illustrated in FIG. 1. However, it will be appreciated by one of ordinary skill in the art that the glucose monitoring system 100 may include one or more sensor 101, transmitter 102, communication link 103, receiver 104, and data processing terminal 105, where each receiver 104 is uniquely synchronized with a respective transmitter 102. Moreover, within the scope of the present invention, the glucose monitoring system 100 may be a continuous monitoring system, or semi-continuous, or a discrete monitoring system.

In one embodiment of the present invention, the sensor 101 is physically positioned in or on the body of a user whose glucose level is being monitored. The sensor 101 may be configured to continuously sample the glucose level of the user and convert the sampled glucose level into a corresponding data signal for transmission by the transmitter 102. In one embodiment, the transmitter 102 is mounted on the sensor 101 so that both devices are positioned on the user's body. The transmitter 102 performs data processing such as filtering and encoding on data signals, each of which corresponds to a sampled glucose level of the user, for transmission to the receiver 104 via the communication link 103.

In one embodiment, the glucose monitoring system 100 is configured as a one-way RF communication path from the transmitter 102 to the receiver 104. In such embodiment, the transmitter 102 transmits the sampled data signals received from the sensor 101 without acknowledgement from the receiver 104 that the transmitted sampled data signals have been received. For example, the transmitter 102 may be configured to transmit the encoded sampled data signals at a fixed rate (e.g., at one minute intervals) after the completion of the initial power on procedure. Likewise, the receiver 104 may be configured to detect such transmitted encoded sampled data signals at predetermined time intervals. Alternatively, the glucose monitoring system 100 may be configured with a bi-directional RF (or otherwise) communication between the transmitter 102 and the receiver 104.

Additionally, in one aspect, the receiver 104 may include two sections. The first section is an analog interface section that is configured to communicate with the transmitter 102 via the communication link 103. In one embodiment, the analog interface section may include an RF receiver and an antenna for receiving and amplifying the data signals from the transmitter 102, which are thereafter, demodulated with a local oscillator and filtered through a band-pass filter. The second section of the receiver 104 is a data processing section which is configured to process the data signals received from the transmitter 102 such as by performing data decoding, error detection and correction, data clock generation, and data bit recovery.

In operation, upon completing the power-on procedure, the receiver 104 is configured to detect the presence of the transmitter 102 within its range based on, for example, the strength of the detected data signals received from the transmitter 102 or a predetermined transmitter identification information. Upon successful synchronization with the corresponding transmitter 102, the receiver 104 is configured to begin receiving from the transmitter 102 data signals corresponding to the user's detected glucose level. More specifically, the receiver 104 in one embodiment is configured to perform synchronized time hopping with the corresponding synchronized transmitter 102 via the communication link 103 to obtain the user's detected glucose level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected glucose level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured glucose level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected glucose levels received from the transmitter 102.

Additionally, the transmitter 102, the receiver 104 and the data processing terminal 105 may each be configured for bi-directional wireless communication such that each of the transmitter 102, the receiver 104 and the data processing terminal 105 may be configured to communicate (that is, transmit data to and receive data from) with each other via the wireless communication link 103. More specifically, the data processing terminal 105 may in one embodiment be configured to receive data directly from the transmitter 102 via the communication link 106, where the communication link 106, as described above, may be configured for bi-directional communication. In this embodiment, the data processing terminal 105 which may include an insulin pump, may be configured to receive the glucose signals from the transmitter 102, and thus, incorporate the functions of the receiver 104 including data processing for managing the patient's insulin therapy and glucose monitoring. In one embodiment, the communication link 103 may include one or more of an RF communication protocol, an infrared communication protocol, a Bluetooth® enabled communication protocol, an 802.11× wireless communication protocol, or an equivalent wireless communication protocol which would allow secure, wireless communication of several units (for example, per HIPPA requirements) while avoiding potential data collision and interference.

Figure 2:
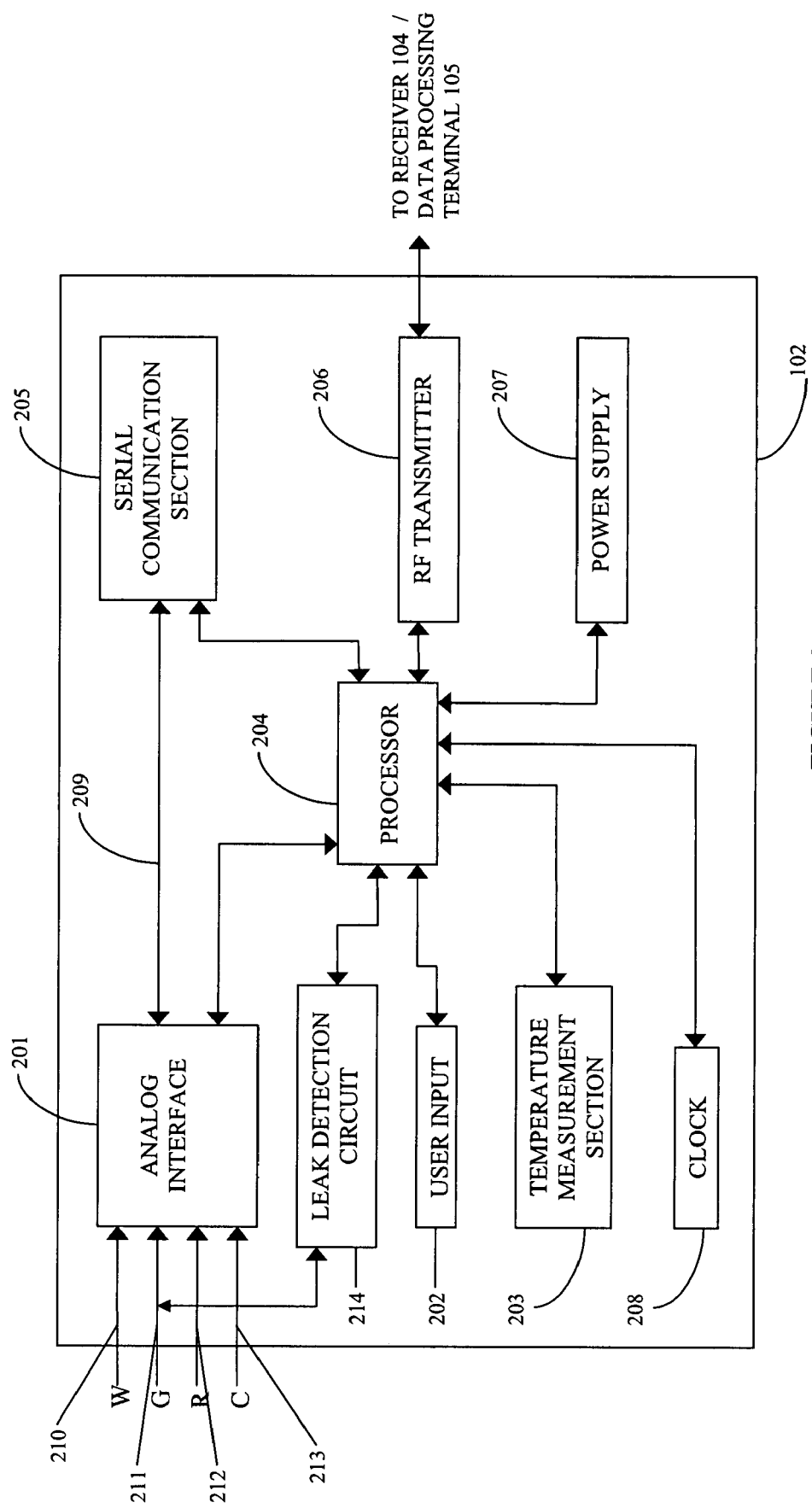
FIG. 2 is a block diagram of the transmitter of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter 102 in one embodiment includes an analog interface 201 configured to communicate with the sensor 101 (FIG. 1), a user input 202, and a temperature measurement section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the transmitter 102 for connection to the sensor unit 101 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter 102 to provide the necessary power for the transmitter 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter 102, while a unidirectional output is established from the output of the RF transmitter 206 of the transmitter 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter 102 for operation upon completion of the manufacturing process as well as for direct communication for diagnostic and testing purposes.

As discussed above, the transmitter processor 204 is configured to transmit control signals to the various sections of the transmitter 102 during the operation of the transmitter 102. In one embodiment, the transmitter processor 204 also includes a memory (not shown) for storing data such as the identification information for the transmitter 102, as well as the data signals received from the sensor 101. The stored information may be retrieved and processed for transmission to the receiver 104 under the control of the transmitter processor 204. Furthermore, the power supply 207 may include a commercially available battery.

The transmitter 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 µA of current. Indeed, in one embodiment, the final step during the manufacturing process of the transmitter 102 may place the transmitter 102 in the lower power, non-operating state (i.e., post-manufacture sleep mode). In this manner, the shelf life of the transmitter 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter 102 in one embodiment may include a rechargeable battery unit that may be recharged by a separate power supply recharging unit so that the transmitter 102 may be powered for a longer period of usage time. Moreover, in one embodiment, the transmitter 102 may be configured without a battery in the power supply section 207, in which case the transmitter 102 may be configured to receive power from an external power supply source (for example, a battery) as discussed in further detail below.

Referring yet again to FIG. 2, the temperature measurement section 203 of the transmitter 102 is configured to monitor the temperature of the skin near the sensor insertion site. The temperature reading is used to adjust the glucose readings obtained from the analog interface 201. The RF transmitter 206 of the transmitter 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Referring yet again to FIG. 2, also shown is a leak detection circuit 214 coupled to the guard electrode (G) 211 and the processor 204 in the transmitter 102 of the data monitoring and management system 100 (FIG. 1). The leak detection circuit 214 in accordance with one embodiment of the present invention may be configured to detect leakage current in the sensor 101 to determine whether the measured sensor data are corrupt or whether the measured data from the sensor 101 is accurate.

Additional detailed description of the continuous glucose monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application, and the disclosures of each of which are incorporated herein by reference for all purposes.

Figure 3:
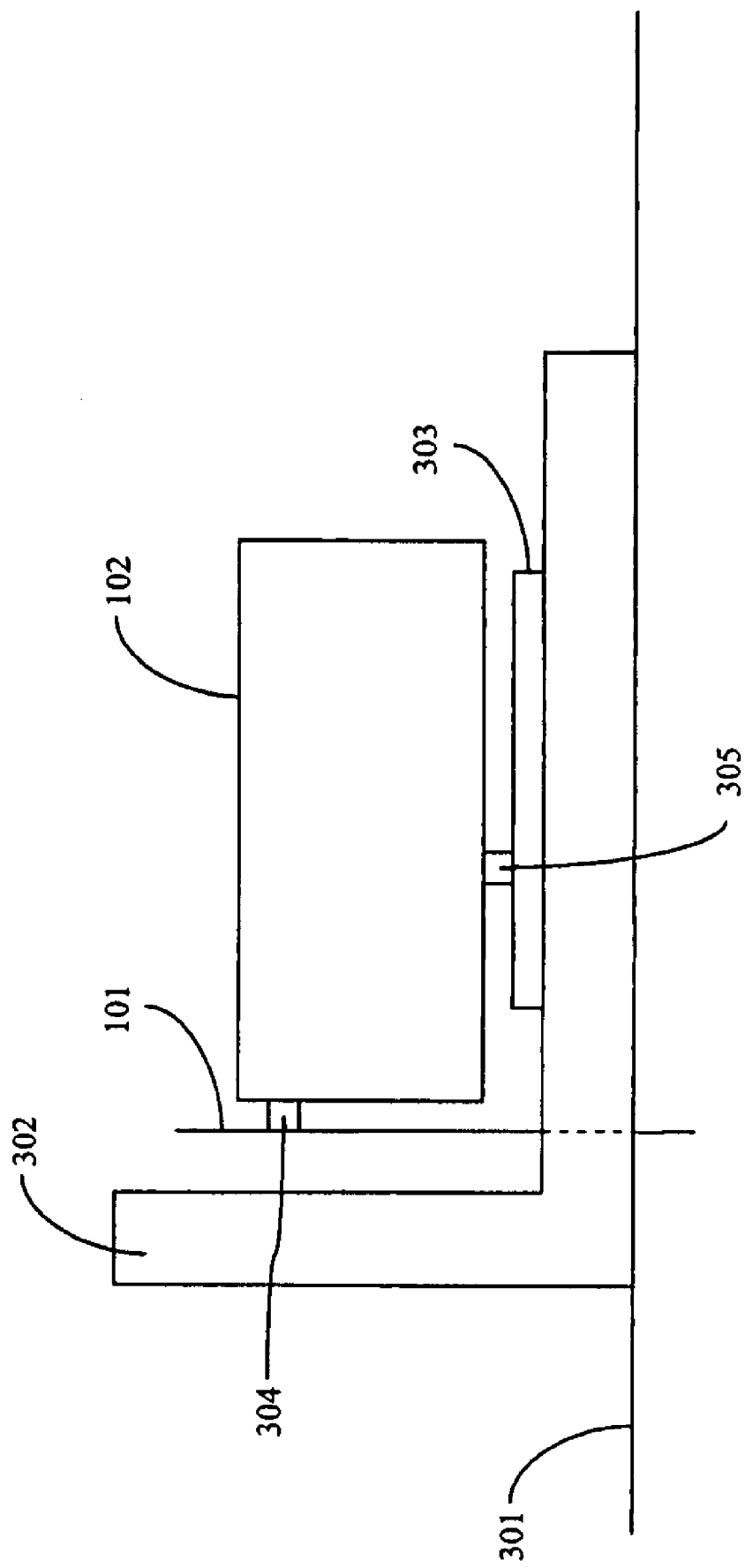
FIG. 3 illustrates a cross sectional view of the transmitter and transmitter mount configuration for providing power to the transmitter in the data monitoring and management system in accordance with one embodiment of the present invention.

FIG. 3 illustrates a cross sectional view of the transmitter and transmitter mount configuration for providing power to the transmitter in the data monitoring and management system in accordance with one embodiment of the present invention. Referring to the Figure, there is shown a transmitter unit mount 302 which is placed on the skin 301 of the patient, and configured to receive a portion of the sensor 101, and the other end portion of the sensor is inserted, e.g., subcutaneously, under the patient's skin 301. Referring to FIG. 3, the transmitter unit mount 302 is configured to receive or "mate" with the transmitter 102 so that the transmitter 102 is in electrical contact with the sensor 101 that extends from the patient's skin 301 at the sensor contact 304. In one embodiment and as discussed above, the sensor contact 304 may be configured to operatively couple the analog interface unit 201 (FIG. 2) of the transmitter 102 with the sensor electrodes and contacts (working electrode 210, guard trace 211, reference electrode 212, and counter electrode 213).

While not shown in the Figure, the transmitter unit mount 302 in one embodiment is firmly affixable onto the patient's skin 301 by an adhesive layer on the surface of the transmitter unit mount 302 that is in contact with the patient's skin 301. In this manner, the patient's movement of the body does not substantially affect the position of the transmitter unit mount 302, and thus the sensor 101 in contact with the transmitter 102. Referring back to FIG. 3, also shown is a power supply 303 (such as, for example, a battery) mounted to the transmitter unit mount 302. In one embodiment, the power supply 303 is positioned to establish electrical contact with the transmitter 102 at the power supply contact 305, when the transmitter is mounted onto the transmitter unit mount 302.

More specifically, in this configuration, the internal power supply 207 (FIG. 2) and/or other components of the transmitter 102 are coupled to the external power supply 303 via the power supply contact 305. In this manner, when the transmitter 102 is mounted to the transmitter unit mount 302, the internal power supply 207 of the transmitter 102 is configured to receive power from the external power supply 303, and thus may be configured to transmit sensor data received from the sensor 101.

Within the scope of the present invention, the external power supply 303 mounted to the transmitter unit mount 302 may include a disposable battery, or a printed battery which may be printed onto the surface of the transmitter unit mount 302 on the surface where the transmitter 102 is configured to physically contact the transmitter unit mount 302.

In a further embodiment, as discussed above, the internal power supply 207 of the transmitter 102 may include a rechargeable battery which may be configured to receive power to recharge from the external power supply 303 mounted to the transmitter unit mount 302, when the transmitter 102 is mounted to the transmitter unit mount 302. In this manner, the external power supply 303 may be configured to provide power to recharge the internal power supply 207 of the transmitter 102, and further, to provide power to the transmitter 102.

Within the scope of the present invention, the rechargeable internal power supply 207 in the transmitter 102 and the external power supply 303 mounted on the transmitter unit mount 302 may include one or more of alkaline, nickel metal hydride, lithium, nickel cadmium, lithium hydride, polymer batteries, polymorphic heavy ion salts, bimetallic interstitial lattice ionic crystals or ferromagnetic materials. Furthermore, in one embodiment, the external power supply 303 may be mounted or coupled to the transmitter unit mount 302 by one of insert molding, welding, casting or printing.

In the manner described above, in accordance with one embodiment of the present invention, a transmitter unit mount 302 may be configured to integrate a power supply 303, such as a battery, that is disposable, so that when the transmitter 102 is mounted, power is provided to the transmitter 102. When the transmitter 102 is dismounted from the transmitter unit mount 302, then the transmitter 102 may be powered off and the transmitter unit mount 302 and the power supply 303 are discarded. The transmitter 102 in one embodiment may also be configured to enter a low power sleep state powered by the remaining charge in the power supply 207 (FIG. 2).

In one embodiment, the power supply 303 which includes disposable batteries can be very small since it is a disposable battery which is to be replaced with each sensor 101 replacement, and thus does not require a large capacity (thus allowing the size of the battery to be small). One example of such disposable battery as power supply 303 is a silver oxide battery.

Within the scope of the present invention, there is also provided an embodiment which includes a second rechargeable battery integrated with the transmitter 102 so that the transmitter 102 may be configured to maintain the RF communication link with the receiver 104 (FIG. 1) and/or the data processing terminal 105 (FIG. 1). In this embodiment, as discussed above, when the transmitter 102 is mounted to the transmitter mount unit 302, the internal power supply 207 (FIG. 2) of the transmitter 102 is configured to recharge from the energy powered by the external power supply 303 of the transmitter unit mount 302.

Figure 4:
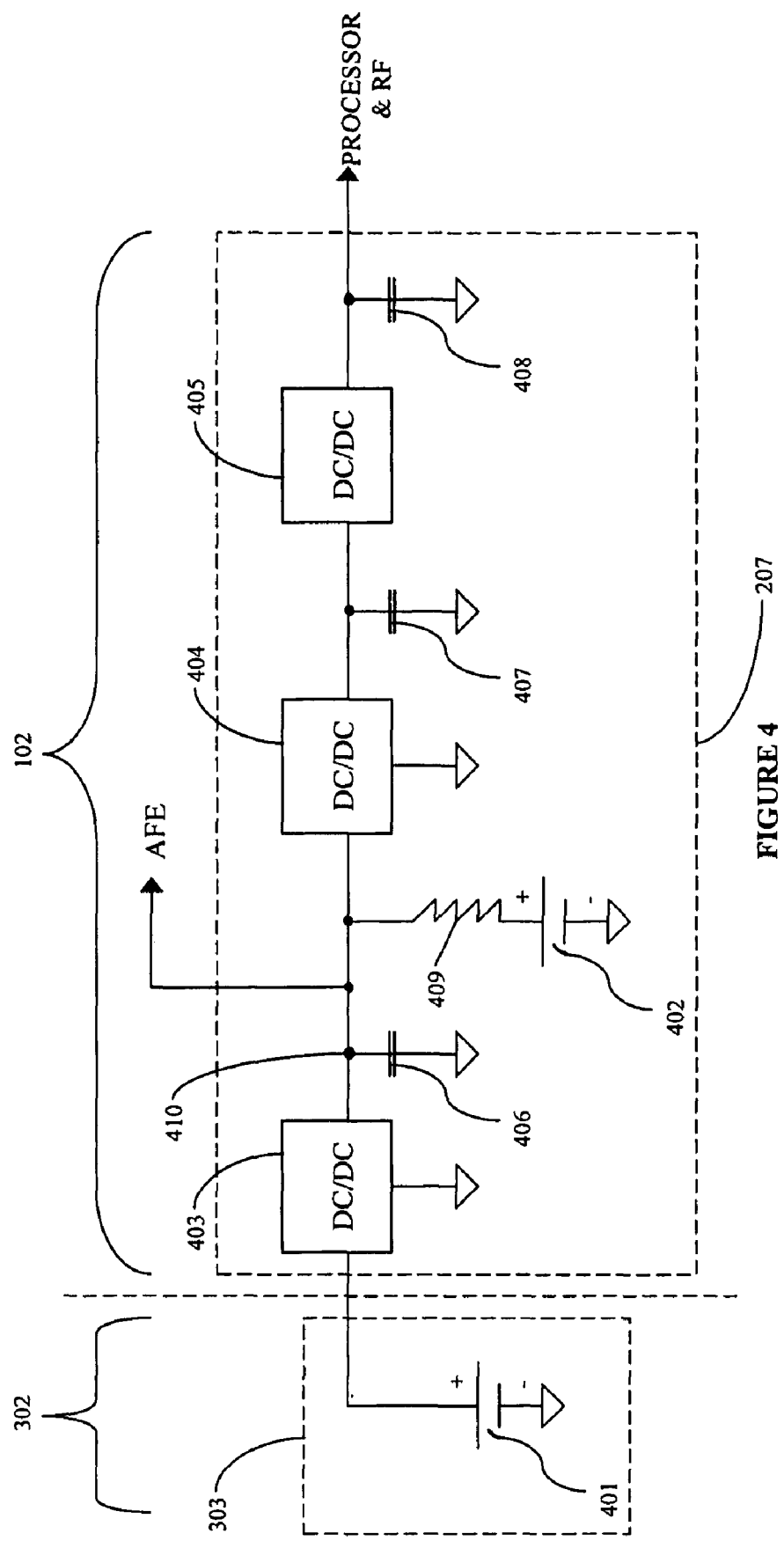
FIG. 4 is a circuit diagram of the energy storage approach for providing power to the transmitter in the data monitoring and management system in accordance with one embodiment of the present invention.

FIG. 4 is a circuit diagram of the energy storage approach for providing power to the transmitter in the data monitoring and management system in accordance with one embodiment of the present invention. Referring to the Figure, there is shown the disposable power supply 401 of the transmitter unit mount 302 which is configured to be replaced with the replacement of the sensor 101 (FIG. 1). Also, shown is the transmitter 102 including, among others, the internal power supply 207, which, in one embodiment, includes a plurality of DC/DC converters 403, 404, 405, each operatively coupled to a respective capacitors 406, 407, 408. Also shown in FIG. 4 is a resistor 409 operatively coupled to a rechargeable battery 402 of the transmitter 102. The rechargeable battery 402 of the transmitter 102 shown in FIG. 4 in one embodiment corresponds to the power supply 207 of the transmitter 102 shown in FIG. 2.

In one embodiment, referring to FIG. 4, when the transmitter 102 is mounted to the transmitter unit mount 302, the power supply 401 of the transmitter unit mount 302 is configured to charge the rechargeable battery 402 of the transmitter 102. The DC/DC converter 403 in one embodiment is configured to boost the voltage signal from power supply 401 (e.g., 1.5 Volts) to the voltage level needed for the processor 204 (FIG. 2) of the transmitter 102 to operate (for example, to 3 Volts). Indeed, as shown in FIG. 4, the voltage level at the Analog Front End (AFE) of the transmitter 102 can be derived from the node 410 shown in the Figure.

Referring back to FIG. 4, in one embodiment, the energy from capacitor 406 and/or from the rechargeable battery 402 of the transmitter 102 may be used to charge the capacitor 407 to a predetermined value (e.g., between a 5 Volt to 35 Volt range) by the DC/DC converter 404 boosting the voltage level to the predetermined range from the 3 Volts at node 410. In one embodiment, both the rechargeable battery 402 and the capacitor 406, or alternatively, the rechargeable battery 402 or the capacitor 406, may be used to charge the capacitor 407, depending upon the various system requirements and the design trade-offs. One example of the capacitor 407 is a Tantalum type capacitor.

Indeed, increasing the voltage from 3 Volts to 30 Volts, for example, provides approximately 100 times the energy storage (since the energy stored in a capacitor is equal to one half of the product of the capacitance multiplied with the capacitor voltage squared—i.e., $\frac{1}{2} CV^2$). Then, referring again to FIG. 4, the stored energy in capacitor 407 is converted by the DC/DC converter 405 and filtered by capacitor 408 to a functional voltage level which the processor 204 of the transmitter 102 may be configured to utilize for the RF transmission operation (e.g., 3.3 Volts or 5 Volts).

As pulsed (or peak) current is drawn by the processor 204 in the transmitter 102, during the RF transmission operations, the voltage across the capacitor 407 drops from a high value towards the minimum value for DC/DC converter operation. In other words, in one embodiment, the capacitor 407 is "trickle charged" at a low current during periods when the pulse current is not active, and when the large peak load occurs, the capacitor 407 is configured to draw charge from the capacitor and not the source.

In this manner, in one embodiment of the present invention, the DC/DC converters 404 and 405 and the corresponding capacitors 407 and 408, are configured to draw a small current from the energy store (e.g., capacitor 406 or the rechargeable battery 402), and to store energy on capacitor 407 that provides a large peak (pulsed) current capability to the processor 204 (FIG. 2) and RF transmitter 206 (FIG 2). This allows low current drive power sources, such as a printed battery or a low current coin-cell battery to power the transmitter 102 in normal operations. For test and configuration purposes, a more robust power source such as a bench power supply may be used to support continuous operation.

Figure 5:
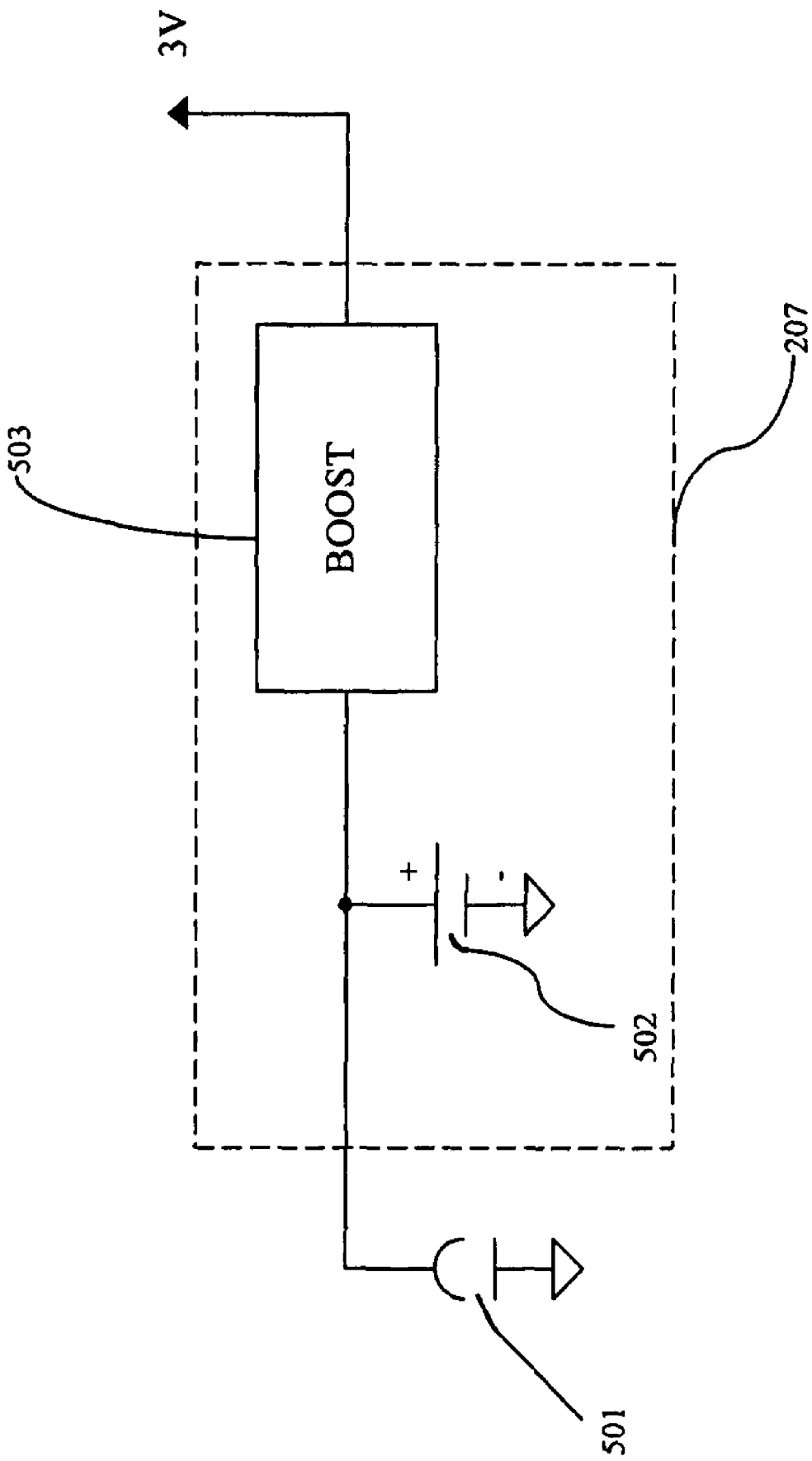
FIG. 5 illustrates another energy storage approach for providing power to the transmitter in the data monitoring and management system in accordance with another embodiment of the present invention.

FIG. 5 illustrates another energy storage approach for providing power to the transmitter in the data monitoring and management system in accordance with another embodiment of the present invention. Referring to the Figure, in one embodiment of the present invention, a single large capacitor (supercap) 501 is used for energy store in the transmitter 102, as opposed to, for example, the capacitor 406 shown in the embodiment in FIG. 4. Moreover, it can be seen that the power supply 502 (e.g., battery) of the transmitter 102 shown in FIG. 5 is similar to the power supply 402 shown in FIG. 4. Further, the boost circuit 503 shown in FIG. 5 in one embodiment corresponds to the DC/DC converter 403 of the embodiment shown in FIG. 4.

Referring back to FIG. 5, the use of the single supercap 501 in parallel with the power supply 502 for energy storage has advantages in terms of size and cost. Moreover, it should be noted that the equivalent series resistance (ESR) of the capacitor is an important design consideration. Indeed, in general, supercaps have a higher ESR which tends to limit the efficiency and effectiveness of the supercap design, especially in cases where the working voltage is greater than 2.5 volts. Moreover, within the scope of the present invention, the battery 502 may need to have relatively high current capacity (for example, compared to the rechargeable battery 402 shown in FIG. 4), due to ESR of the supercap 501.

In one embodiment, the supercap 501 may be configured to provide a low internal resistance energy source that allows a large current to be delivered to the transmitter unit 102. It is difficult to achieve this directly from a battery. Small batteries generally cannot deliver a high current, so for a relatively small and compact size design such as for the design of the transmitter unit 102, this provides a significant advantage. Also, while at low temperatures the internal resistance of batteries increase, this may be mitigated by using a supercap or other type of storage capacitor connected in parallel with the battery.

In the manner described above, an apparatus including a data transmission unit in one embodiment includes a sensor, a transmitter base including a first power supply, and a transmitter unit coupled to the transmitter base, the transmitter unit including a second power supply, the transmitter unit further configured to establish electrical contact with the sensor, and further, where the transmitter unit is configured to draw power from one or more of the first power supply and the second power supply.

The sensor may in one embodiment include an analyte sensor transcutaneously positioned in a patient such that at least a portion of the analyte sensor is in fluid contact with a biological fluid of the patient.

Moreover, the first power supply may include a disposable battery, such as, for example, a silver oxide battery, and where the second power supply may include a rechargeable battery configured to selectively draw power from the first power supply.

In a further embodiment, each of the first power supply and the second power supply may include one of a disposable battery or a rechargeable battery.

The transmitter unit in one embodiment may be configured to transmit one or more signals, where the one or more signals correspond to a respective one or more signals received from the sensor, and where the transmitter unit may be configured for wireless communication or may include a physical connection. Additionally, the one or more signal received from the sensor corresponds to one or more analyte levels (for example, glucose levels) of a patient detected by the sensor.

An apparatus in a further embodiment of the present invention includes a sensor transcutaneously positioned in a patient, a transmitter base including a transmitter base power supply, a transmitter unit coupled to the transmitter base power supply of the transmitter base, the transmitter base power supply of the transmitter base configured to provide power to the transmitter unit, the transmitter unit further configured to establish electrical contact with the sensor.

In one embodiment, the sensor may include an analyte sensor where least a portion of the analyte sensor is in fluid contact with a biological fluid of the patient, where the biological fluid includes one of interstitial fluid, lactate or oxygen.

Moreover, the apparatus in one embodiment may also include a receiver unit configured to receive the one or more signals from the transmitter unit.

In still a further embodiment, the transmitter base power supply may include a disposable battery such as for example, a silver oxide battery.

Also, the transmitter unit may further include a transmitter unit power supply disposed substantially within the housing of the transmitter unit, where the transmitter unit power supply may in one embodiment include a rechargeable battery, and also, where the rechargeable battery may be configured to substantially draw power from the transmitter base power supply.

An apparatus in still a further embodiment includes a rechargeable battery, and a transmitter unit coupled to the rechargeable battery configured to draw power from the rechargeable battery.

A method in still another embodiment of the present invention includes the steps of providing a power supply to a transmitter mount, operatively coupling a transmitter unit to the transmitter mount such that the transmitter unit is in electrical contact with the power supply, operatively coupling a transcutaneously positioned analyte sensor to the transmitter unit such that the transmitter unit receives one or more signals corresponding to one or more analyte levels from the sensor.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus including a data transmission unit, comprising:
   a sensor including an electrical contact portion and an insertion portion, wherein the insertion portion is adapted for transcutaneous positioning under a skin surface of a patient and for contacting biological fluid under the skin surface, the sensor configured to generate multiple analyte related signals during a sensing time period;
   a transmitter unit mount including a disposable battery and an adhesive layer provided on a mount surface of the transmitter unit mount, the transmitter unit mount configured to be positioned on the skin surface of a patient such that the adhesive layer is in contact with the skin surface and retains the mount surface of the transmitter unit mount in a substantially fixed position on the skin surface, the transmitter unit mount receiving the electrical contact portion of the sensor when the insertion portion of the sensor is positioned under the skin surface and in fluid contact with the analyte; and
   a transmitter unit received by the transmitter unit mount, the transmitter unit including a rechargeable battery, the transmitter unit further configured to establish electrical contact with the electrical contact portion of the sensor, and further, wherein the transmitter unit is configured to draw power from one or more of the disposable battery or the rechargeable battery.

2. The apparatus of claim 1 wherein the sensor is configured to detect an analyte of the patient.

3. The apparatus of claim 1 wherein the disposable battery includes a silver oxide battery.

4. The apparatus of claim 1 wherein the transmitter unit is configured to transmit one or more signals, where the one or more signals corresponds to a respective one or more signals received from the sensor.

5. The apparatus of claim 4 wherein the transmitter unit is configured to wirelessly transmit the one or more signals.

6. The apparatus of claim 4 wherein the one or more signal received from the sensor correspond to one or more analyte levels of the patient detected by the sensor.

7. The apparatus of claim 6 wherein the one or more analyte levels include glucose levels.

8. The apparatus of claim 1 wherein the electrical contact between the transmitter unit and the sensor is terminated after a predetermined time period when the transmitter unit is decoupled from the transmitter unit mount.

9. An apparatus, comprising:
   a sensor including an electrical contact portion at a first end and an insertion portion at a second end, the first and second ends of the sensor substantially defining a length of the sensor, the insertion portion of the sensor adapted to be transcutaneously positioned in a patient so as to be in continuous fluid contact with a biological fluid under a skin surface of the patient during a sensing time period, the sensor configured to generate multiple analyte related signals during the sensing time period;
   a transmitter base including a transmitter base power supply, the transmitter base including a base surface having an adhesive layer, the adhesive layer in contact with the skin surface of the patient when the transmitter base is positioned on the skin surface of the patient, the transmitter base having a housing; and
   a transmitter unit having a housing which mates with the transmitter base housing, the transmitter unit coupled to the transmitter base power supply of the transmitter base, the transmitter base power supply of the transmitter base configured to provide power to the transmitter unit, the transmitter unit further configured to establish electrical contact with the electrical contact portion of the sensor when mated with the transmitter housing;
   wherein the adhesive layer retains the transmitter base and the transmitter unit in a substantially fixed position on the skin surface when the transmitter unit housing is mated with the transmitter base.

10. The apparatus of claim 9 wherein the sensor is configured to detect an analyte of the patient.

11. The apparatus of claim 10 wherein the biological fluid includes one of interstitial fluid, lactate or oxygen.

12. The apparatus of claim 9 wherein the transmitter unit is configured to transmit one or more signals, where the one or more signals corresponds to a respective one or more signals received from the sensor.

13. The apparatus of claim 12 further including a receiver unit in signal communication with the transmitter unit.

14. The apparatus of claim 9 wherein the transmitter base power supply includes a disposable battery.

15. The apparatus of claim 14 wherein the disposable battery includes a silver oxide battery.

16. The apparatus of claim 9 wherein the transmitter unit further includes a transmitter unit power supply disposed substantially within the housing of the transmitter unit.

17. The apparatus of claim 16 wherein the transmitter unit power supply includes a rechargeable battery, and further wherein the rechargeable battery is configured to substantially draw power from the transmitter base power supply.

18. The apparatus of claim 9 wherein the electrical contact between the transmitter unit and the sensor is terminated after a predetermined time period when the transmitter unit is decoupled from the transmitter base.

19. An apparatus, comprising:
   a housing;
   an analyte sensor coupled to the housing and configured to generate multiple analyte related signals during the sensing time period;
   a rechargeable battery provided within the housing;
   a transmitter unit provided within the housing and coupled to the rechargeable battery, the transmitter unit configured to draw power from the rechargeable battery to transmit the multiple analyte related signals to a remote location; and
   a transmitter unit mount including a disposable battery disposed therein, the transmitter unit mount configured to removably mate with the housing, the transmitter unit mount including an adhesive layer provided on a mount surface for adhering to a skin surface such that the movement of the skin surface does not substantially affect the position of the transmitter unit mount adhered to the skin surface;
   wherein the rechargeable battery is configured to recharge from the disposable battery disposed in the transmitter unit mount when the housing is mated with the transmitter unit mount.

* * * * *

UNITED STATES PATENT AND TRADEMARK OFFICE
CERTIFICATE OF CORRECTION

| | | |
|---|---|---|
| PATENT NO. | : 7,756,561 B2 | Page 1 of 1 |
| APPLICATION NO. | : 11/240273 | |
| DATED | : July 13, 2010 | |
| INVENTOR(S) | : Christopher Reggiardo et al. | |

It is certified that error appears in the above-identified patent and that said Letters Patent is hereby corrected as shown below:

Column 1, line 8, replace "analayte" with --analyte--.
Column 1, line 35, replace "e.g," with --e.g.,--.
Column 1, line 61, replace "compact, lightweight" with --compact and lightweight--.
Column 3, line 5, replace "acetyl choline" with --acetylcholine--.
Column 5, line 2, replace "HIPPA" with --HIPAA--.
Column 8, line 1, replace "power supply 303" with --power supply 303,--.
Column 8, line 2, replace "batteries" with --batteries,--.
Column 9, line 14, replace "energy on capacitor" with --energy in capacitor--.

Signed and Sealed this
Thirty-first Day of May, 2011

David J. Kappos
*Director of the United States Patent and Trademark Office*